United States Patent
Oguchi et al.

(10) Patent No.: US 9,216,946 B2
(45) Date of Patent: Dec. 22, 2015

(54) METHOD OF PRODUCING BASIC AMINO ACID OR BASIC AMINO ACID SALT

(71) Applicant: AJINOMOTO CO., Inc., Chuo-ku (JP)

(72) Inventors: Yuta Oguchi, Kawasaki (JP); Gaku Hamada, Saga (JP); Kazuhiro Hasegawa, Kawasaki (JP)

(73) Assignee: AJINOMOTO CO., INC., Chuo-ku (JP)

( * ) Notice: Subject to any disclaimer, the term of this patent is extended or adjusted under 35 U.S.C. 154(b) by 0 days.

(21) Appl. No.: 14/419,271

(22) PCT Filed: Jul. 24, 2013

(86) PCT No.: PCT/JP2013/004496
§ 371 (c)(1),
(2) Date: Feb. 3, 2015

(87) PCT Pub. No.: WO2014/020866
PCT Pub. Date: Feb. 6, 2014

(65) Prior Publication Data
US 2015/0183725 A1      Jul. 2, 2015

Related U.S. Application Data

(60) Provisional application No. 61/679,324, filed on Aug. 3, 2012.

(51) Int. Cl.
C07C 227/18    (2006.01)
C07C 227/40    (2006.01)
C07C 227/42    (2006.01)

(52) U.S. Cl.
CPC ............. *C07C 227/18* (2013.01); *C07C 227/40* (2013.01); *C07C 227/42* (2013.01)

(58) Field of Classification Search
None
See application file for complete search history.

(56) References Cited

U.S. PATENT DOCUMENTS

| 4,835,309 A | 5/1989 | Jaffari et al. | |
| 2002/0153261 A1* | 10/2002 | Hasegawa et al. | 205/422 |
| 2005/0284813 A1* | 12/2005 | Kusunose et al. | 210/638 |

(Continued)

FOREIGN PATENT DOCUMENTS

| EA | 0 714 884 A1 | 6/1996 |
| EA | 1 995 322 A1 | 11/2008 |
| JP | 52-31020 A | 3/1977 |

(Continued)

OTHER PUBLICATIONS

International Search Report Issued Oct. 22, 2013 in PCT/JP13/004496 Filed Jul. 24, 2013.

(Continued)

*Primary Examiner* — Karl J Puttlitz
(74) *Attorney, Agent, or Firm* — Oblon, McClelland, Maier & Neustadt, L.L.P.

(57) ABSTRACT

[Problem] It is to provide a method of producing basic amino acid or basic amino acid salt suitable for each use for medicine, industrial use, feed, food additive and the like, by a simple method to remove HCl from HCl salt of basic amino acid efficiently.
[Solving Means]
The above problem is solved by a method of producing a basic amino acid or a basic amino acid salt which comprises allowing to coexist a weak acid in a basic amino acid HCl salt solution, when the solution is dechlorinated using an anion-exchange resin.

12 Claims, 2 Drawing Sheets

(56) References Cited

U.S. PATENT DOCUMENTS

| | | |
|---|---|---|
| 2009/0075348 A1 | 3/2009 | Han et al. |
| 2009/0082594 A1 | 3/2009 | Murata et al. |

FOREIGN PATENT DOCUMENTS

| | | |
|---|---|---|
| JP | 57-35549 A | 2/1982 |
| JP | 58 210027 | 12/1983 |
| JP | 60 256392 | 12/1985 |
| JP | 62-174043 A | 7/1987 |
| JP | 2 6443 | 1/1990 |
| WO | 2004 061114 | 7/2004 |
| WO | WO 2006/001345 A1 | 1/2006 |
| WO | WO 2006/001378 A1 | 1/2006 |
| WO | WO 2006/051940 A1 | 5/2006 |

OTHER PUBLICATIONS

Supplementary European Search Report issued Apr. 28, 2015 in Patent Application No. 13826103.7.

Antonio de Lucas, et al., "Ion Exchange Kinetics of DL-Lysine Monohydrochloride on Amberlite IRA-420" Solvent Extraction and Ion Exchange, vol. 14, No. 6, XP008175843, Jan. 1, 1996, pp. 1115-1135.

* cited by examiner

METHOD OF PRODUCING BASIC AMINO ACID OR BASIC AMINO ACID SALT

TECHNICAL FIELD

This invention relates to a method of removing hydrochloric acid (hereinafter referred to as HCl) from a basic amino acid hydrochloric acid salt (hereinafter referred to as HCl salt of basic amino acid).

BACKGROUND ART

There are various basic amino acids, and representative ones are lysine, arginine, histidine, ornithine, and the like. These basic amino acids are commonly manufactured in a form of HCl salt.

On the other hand, basic amino acids are also utilized for medicinal use, and in this case, HCl salt must be removed, because it adversely affects on human body. Moreover, they are also utilized for industrial use, use for feed, use for food additives, and the like, in addition to the medicinal use, and, it is required to be commercialized in a form of a preferable weak acid salt, according to the use.

Various methods are known for manufacturing basic amino acid by removing HCl from the HCl salt of basic amino acid.

For example, it is disclosed in Example 1 of Patent Document 1 that a method of adding sulfuric acid to L-Lysine fermentation broth to make it acidic property, feeding the broth to strongly acidic cation-exchange resin in ammonium form to adsorb L-lysine on it, and eluting the adsorbed L-lysine by aqueous ammonia solution.

Patent Document 2 discloses a method of obtaining basic amino acid solution by subjecting basic amino acid salt solution to electrodialysis in an electrodialysis vessel containing a combination of cation-exchange membrane and anion-exchange membrane.

Non-Patent Document 1 discloses that adsorption behavior of L-lysine HCl salt on anion-exchange resin was studied, and dechlorination from L-lysine was attempted by varying adsorption equilibrium with controlling temperature.

PRIOR ART DOCUMENTS

Patent Documents

Patent Document 1: JP4-134054 A
Patent Document 2: JP2002-284749 A

Non-Patent Document

Non-Patent Document 1: Lucas et al., "ION EXCHANGE KINETICS OF DL-LYSINE MONOHYDROCHLORIDE ON AMBERLITE IRA-420", Solvent Extraction and Ion Exchange, 1996, 14 (6), PP 1115-1135

SUMMARY OF THE INVENTION

Problems to be Solved by the Invention

The method of Patent Document 1 has a problem in cost and load with waste water, because an equipment for recovery of aqueous ammonia, which is the eluent, is needed, and required resin volume and volume of wash water accompanied therewith increase in order to ensure sufficient adsorption capacity.

The method of Patent Document 2 requires cost for equipments, and therefore, is unsuitable for the production of basic amino acid.

In the temperature control method of Non-Patent Document 1, break through point of chloride ion (hereinafter referred to as Cl or $Cl^-$) was very fast, and therefore, the yield of lysine was very small, in every case.

An object of the invention is to provide a method of producing basic amino acid or basic amino acid salt suitable for respective uses for medicines, in industry, for feeds, for food additives and the like, by removing HCl efficiently from the HCl salt of basic amino acid by a simple method.

Means for Solving Problems

The inventors investigated eagerly in order to solve the above problems, and first, investigated as to the dechlorination using a weakly basic anion-exchange resin. However, Cl adsorbed on this resin was little. They considered that the pH of basic amino acid solution was raised through the dechlorination and thereby, ion-exchange ability of the weakly basic anion-exchange resin does not work.

Thereupon, the dechlorination was next investigated using a strongly basic anion-exchange resin. As a result, the dechlorination could be achieved, but another problem occurred that the yield of basic amino acid was decreased by the simultaneous adsorption of the basic amino acid. They considered that this was caused by that the pH of the basic amino acid solution was raised by the dechlorination, and thereby, the basic amino acid was converted to anion to be adsorbed.

Therefore, the inventors were further investigated, and arrived to consider that when a weak acid is allowed to exist in the HCl salt of basic amino acid solution, the pH rise of the basic amino acid solution caused by the dechlorination is depressed by the weak acid to allow to continue exhibition of the ion-exchange ability of the anion-exchange resin, and the adsorption of the basic amino acid by its conversion to anion can be prevented.

The present invention was made based on such a conception, and provides a method of producing a basic amino acid or a basic amino acid salt which comprises allowing to coexist a weak acid in a basic amino acid HCl salt solution, when the solution is dechlorinated using an anion-exchange resin.

Effects of the Invention

According to the invention, HCl can be removed from the HCl salt of basic amino acid solution efficiently by a simple method to produce basic amino acid and amino acid salt suitable for various uses, such as medicinal use, industrial use, use for feed, and use for food additive.

MODE FOR CARRYING OUT THE INVENTION

Figure 1:
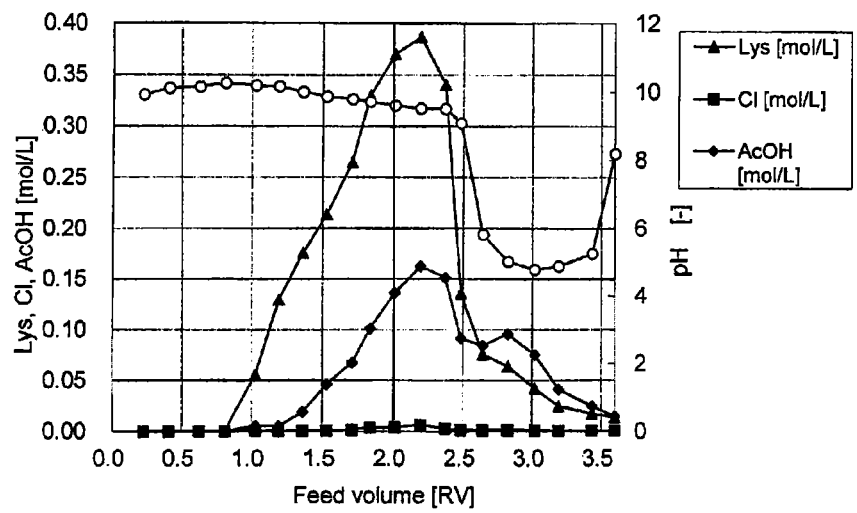
FIG. 1 A graph indicating a break through curve of a L-lysine HCl salt solution to which acetic acid was added, which is an example of the invention, when it was passed through a strongly basic anion-exchange resin.

The type of the basic amino acid of which dechlorination is conducted by the method of the invention is not limited, but illustrative are lysine, arginine, histidine, ornithine, hydroxylysine, and so on. Although there are optical isomers in the basic amino acid, either one may be applicable, and it may be a racemate. The origin of the basic amino acid is also not particularly limited.

The HCl in the basic amino acid HCl salt is generally one molecule per one molecule of the basic amino acid, but is not limited thereto. The HCl may be two molecules, three molecules or the like, or may be a quantity having a point such as 0.5 molecule.

The HCl salt of basic amino acid is allowed to contact with anion-exchange resin in a form of solution. The quality and purity of the HCl salt of basic amino acid solution is not particularly limited, but may be in any grade, such as in a form of fermentation broth, for feed, for industrial use, for food additive or for medicine.

The concentration of the basic amino acid is not limited within the range capable of treating by anion-exchange resin, but for example, is 1 g/dl to solubility in saturation, usually about 5 to 15 g/dl.

The weak acid, which is allowed to coexist with the basic amino acid, is an acid having a selectivity coefficient to anion-exchange resin smaller than that of hydrochloric acid, and after the dechlorination, the weak acid can keep the basic amino acid at its isoelectric point or lower than that. Furthermore, as the weak acid, it is preferred to select a desirable weak acid according to its use, such as for medicine, for industrial use, for feed or for food additive. The weak acid may be either of organic acid or inorganic acid. As examples of the organic acid, acetic acid, benzoic acid, caproic acid, formic acid, valeric acid, lactic acid, propionic acid, butyric acid, aspartic acid, glutamic acid and the like can be listed, and as examples of the inorganic acid, carbonic acid, iodic acid, fluorine and the like can be listed. Examples of the selectivity coefficient to Duolite A–101D in $OH^-$ form are shown below: $Cl^-=22$, $HCO_3^-=6.0$, $IO_3^-=5.5$, $HCOO^-=4.6$, $CH_3COO^-=3.2$, $CH_3CH_2COOO^-=2.6$, $F^-=1.6$ The amount of the weak acid in the solution of the HCl salt of basic amino acid is an amount capable of keeping a pH of the solution at the isoelectric point of the basic amino acid or lower than that, preferably lower than the isoelectric point by 1 to 2, after HCl was adsorbed on anion-exchange resin, and usually, it is preferred that the acid-base equivalent is made 0.8 equivalence of HCl or more, preferably about 0.8-2.0 equivalences, more preferably about 1.0-1.2 equivalences. The amount of the weak acid includes the amount already contained in the HCl salt of basic amino acid solution as a part, and is adjusted by newly adding the shortage amount.

A preferred pH of the HCl salt of basic amino acid solution is pH 0-9. Usually, it is enough in a state that the HCl salt of basic amino acid is dissolved as it is.

The type of the anion-exchange resin is not particularly restricted, but may be any type of strongly basic anion-exchange resin, weakly basic anion-exchange resin or the like. The form of the anion-exchange resin is also not restricted, but to use in $OH^-$ form is preferred, and for that purpose, the resin is regenerated prior to use.

The method of dechlorinating the HCl salt of basic amino acid solution by using anion-exchange resin can be carried out similar to the conventional operation method of using an ion-exchange resin.

Namely, the conventional process of using an ion-exchange resin is fundamentally composed of three steps of adsorption-elution-regeneration. In the invention, adsorption of Cl ion is carried out in the adsorption step, and elution of the adsorbed Cl is carried out in the elution step. The eluent may be any one capable of eluting the Cl, and sodium hydroxide, sodium carbonate, ammonia and the like can be used. In the case of using OH form of anion-exchange resin in the adsorption step and using an alkali hydroxide is used as the eluent, regeneration is achieved during the elution process simultaneously.

The resin column packed with anion-exchange resin used in the invention may be one, but to use two or more columns is preferred in practical viewpoint. Thereby, continuous production is possible by allotting separate step to each column and transferring the step successively. Particularly, a system of connecting two or more columns in series at each step is preferred, and thereby, exchange capacity of anion-exchange resin can be utilized efficiently at the maximum.

Feed rate of the HCl salt of basic amino acid solution and eluent may be set according to conventional manner, and they are commonly set based on the break through point as a criterion.

According to the invention, 98.5 mol % or more, preferably 99.9 mol % or more of Cl can be removed from the HCl salt of basic amino acid. In the case of lysine, Cl/Lys can be made 1.5 mol % or less, preferably 0.01 mol % or less.

The solution obtained by removing HCl from the HCl salt of basic amino acid solution contains the weak acid used in the invention. The weak acid may be removed, but if the weak acid is favorable or not harmful in the use of the final product, the solution may be used as it is.

As the method of obtaining basic amino acid though the basic amino acid weak acid salt solution using anion-exchange resin from the HCl salt of basic amino acid solution, there is a method of utilizing carbonic acid as the weak acid.

When the weak acid is carbonic acid, basic amino acid can be obtained through decarbonation treatment. A specific decarbonation treatment can be conducted by evaporation operation or the like to remove it easily by releasing as carbon dioxide gas. Especially, evaporation operation under reduced pressure is preferred because of depressing decomposition of basic amino acid caused by heating. The type and structure of evaporation are not particularly limited, and for example, vertical short tube type evaporation, falling type thin film evaporator, forced circulation type evaporator, etc. are applicable. The evaporator may be single-effect or multi-effect. The evaporation operation may be conducted according to conventional conditions, and by controlling the inside pressure of evaporator to 30-250 hPa, preferably 30-150 hPa, carbonic acid can be removed efficiently with depressing decomposition of basic amino acid.

The basic amino acid weak acid salt solution and the basic amino acid solution obtained by removing the weak acid may be either used as is in the form of solution or used in the form of crystals, according to their uses.

In the case of the crystal form, there are crystallization method and direct drying method. The crystallization can be conducted, for example, by concentration, cooling, adding poor solvent, such as organic solvent, or a combination there of, and the direct drying can be conducted, for example, by spray drying or freeze drying, and whichever method may be applied.

In the case of concentration under reduced pressure, recovery ratio can be improved by cooling the resulting concentrated solution to a definite temperature, for example, to 10° C.-30° C., preferably 10-15° C. The recovery ratio can be further improved by adding organic solvent to the resulting concentrates. Illustrative of the organic solvent are methanol, ethanol, 2-propanol and so on.

Crystals of amino acid weak acid salt can be obtained by solid-liquid separation by the operation of centrifugation on the like of the concentrates containing crystals.

Impurities adhering on the surface of the separated crystals may be removed by washing with for example, water, saturated solution of the basic amino acid weak acid salt, organic solvent of methanol, ethanol or 2-propanol.

The separated crystals are dried by fluidized bed drying, reduced pressure drying, tray drying or the like to obtain basic amino acid crystals or basic amino acid salt crystals.

EXAMPLES

Example 1

As the ion-exchange resin, 250 ml of strongly basic amino-exchange resin (Dowex marathon A2, product of Dowex Co., Type II, 1.2 eq/L) was packed in a column, and was regenerated by feeding 3 RV of 1.5 N NaOH, followed by washing with 4 RV of water. The ion-exchange resin was in OH form.

The feed solution was prepared by dissolving L-lysine HCl salt (for feed) in water, and adding equimolar acetic acid with L-lysine (therefore equivalent mole with HCl). The concentration of L-lysine was 5.0 g/dL.

1.6 RV of the feed solution was fed at SV=1 from the top of the above column, followed by washing with 2 RV of water.

The variations of L-lysine concentration (▲), Cl concentration (■), acetic acid concentration (♦) and pH (○) of the effluent solution passed through the column and steamed out from the bottom were measured to obtain a graph shown in FIG. 1.

The obtained results were L-lysine yield of 81%, Cl/L-Lys of the effluent solution=1.5 mol %, and acetic acid yield of 35.5%. The L-lysine yield was 80% or more, and 98.5 mol % of Cl was removed, but considerable amount of acetic acid was simultaneously adsorbed. It was also found that the yield of acetic acid increases with increasing the adsorption amount of Cl due to the low selectivity coefficient of acetic acid to anion-exchange resin compared with Cl. Since L-lysine acetic acid can be supplied to the market by compensating the shortage of acetic acid, there is no problem.

Example 2

As the ion-exchange resin, 200 ml of weakly basic anion-exchange resin (LEWATIT (old trade name: IONAC) A-365, product of LANXESS Co., 3.5 eq/L) was packed in a column, and was regenerated by feeding 4 RV of 1.5 N NaOH, followed by washing with 4 RV of water. The ion-exchange resin was in OH form.

The feed solution was prepared by dissolving L-lysine HCl salt (for feed) in water, and adding equimolar acetic acid with L-lysine. The concentration of L-lysine was 7.0 g/dL.

3.7 RV of the feed solution was fed at SV=1 from the top of the above column, followed by washing with 1.5 RV of water.

Figure 2:
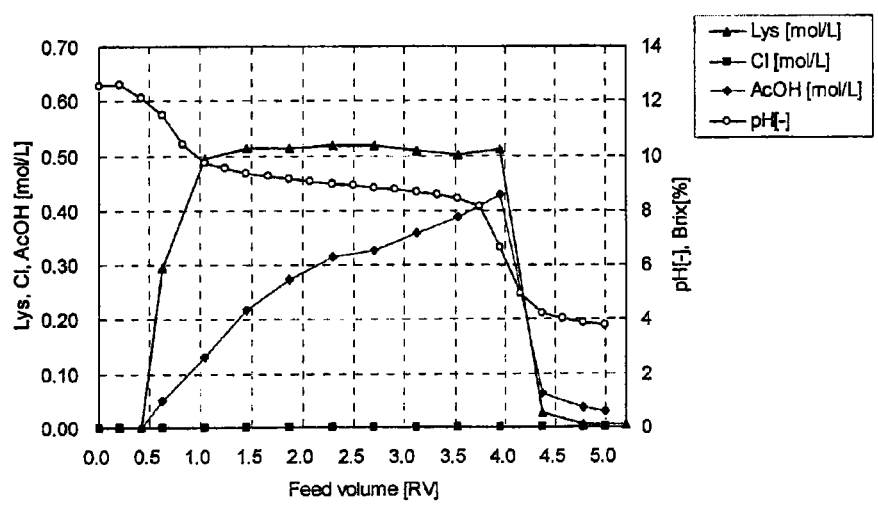
FIG. 2 A graph indicating a break through curve, when the same was passed through a weakly basic anion-exchange resin.

The variations of L-lysine concentration (▲), Cl concentration (■), acetic acid concentration (♦) and pH (○) of the effluent solution passed through the column and steamed out from the bottom were measured to obtain a graph shown in FIG. 2.

The obtained results were L-lysine yield of 98.6%, Cl/L-Lys of the effluent solution=0.03 mol %, and acetic acid yield of 75.7%. The L-lysine yield was 98% or more, and 99.97 mol % of Cl was removed, but adsorption of acetic acid also occurred. It was also found that the yield of acetic acid increases with increasing the adsorption amount of Cl due to the low selectivity coefficient of acetic acid to anion-exchange resin compared with Cl. Since L-lysine acetic acid can be supplied to the market by compensating the shortage of acetic acid, there is no problem.

Examples 3

To the above effluent solution obtained by the method of Example 2, acetic acid was added so as to become 1.0 molar equivalent with L-lysine, and decolored by activated carbon, followed by filtration. The filtrate was concentrated to 95 g/dL L-lysine under reduced pressure, cooled to 15° C., and crystals were separated by centrifugation. The resulting crystals ware washed with 100% methanol, and dried under reduced pressure to obtain L-lysine acetic acid salt product. The recovery of the product from the feed solution (yield of L-lysine) was 57.6%. The purity of the product was examined according to the method described in Japanese Pharmacopoeia, 16th Revision (pp 1385-1386), and found to be 100%.

Comparative Example 1

As the ion-exchange resin, 200 ml of weakly basic anion-exchange resin (LEWATIT (old trade name: IONAC) A-365, product of LANXESS Co., 3.5 eq/L) was packed in a column, and was regenerated by feeding 4 RV of 1.7N-NaOH, followed by washing with 5 RV of water. The ion-exchange resin was in OH form.

The feed solution was prepared by dissolving L-lysine HCl salt (for feed) in water. The concentration of L-lysine was 5.1 g/dL. 9.5 RV of the feed solution was fed at SV=1 from the top of the above column, followed by washing with 2.5 RV of water.

Figure 3:
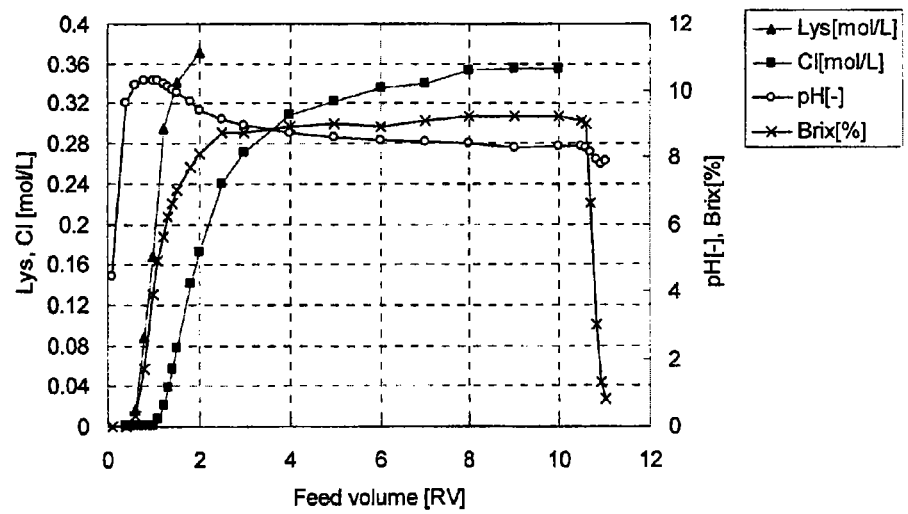
FIG. 3 A graph indicating a break through curve of the L-lysine HCl salt solution to which weak acid was not added, when it was passed through the weakly basic anion-exchange resin.

The variation of L-lysine concentration (▲), Cl concentration (■), pH (○) and Brix (X) of the effluent solution streamed out from the bottom of the column were measured to obtain a graph shown in FIG. 3.

As a result, it was found that adsorption of Cl on the anion-exchange resin was little. It is considered that, in the initial stage where only a small amount of Cl was adsorbed, pH was immediately raised, and thereby, the weakly basic anion-exchange resin did not work ion-exchange action, because the dissociation of ion-exchange group of the weakly basic anion-exchange resin occurs at a pH 9 or higher, whereas the isoelectric point of L-lysine is 9.79.

Comparative Example 2

From the result of Comparative Example 1, dechlorination by strongly basic anion-exchange resin was investigated of which dissociation of ion-exchange group does not depend on pH.

As the ion-exchange resin, 250 ml of strongly basic anion-exchange resin (Dowex marathon A2, product of Dowex Co., type II, 1.2 eq/L) was packed in a column, and was regenerated by feeding 3 RV of 1.5 N NaOH, followed by washing with 4 RV of water. The ion-exchange resin was in OH form.

The feed solution was prepared by dissolving L-lysine HCl salt (for feed) in water. The concentration of L-lysine was 5.0 g/dL.

1.6 RV of the feed solution was fed at SV=1 from the top of the above column, followed by washing with 4 RV of water.

Figure 4:
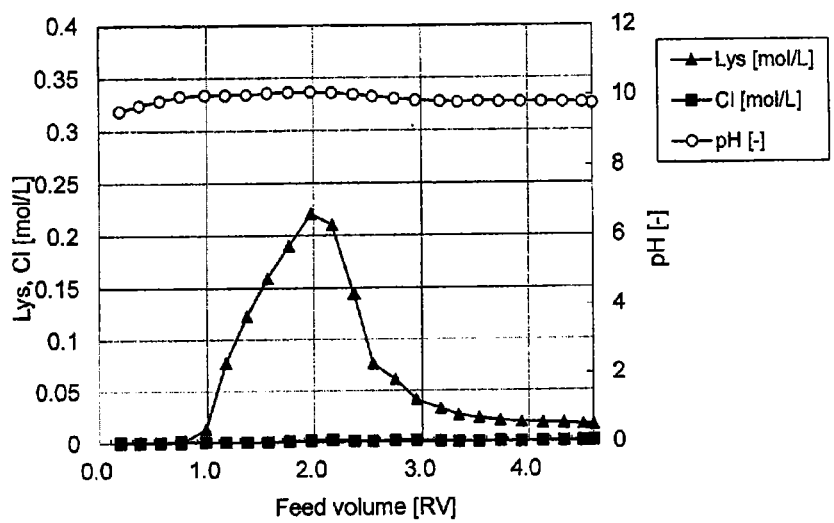
FIG. 4 A graph indicating a break through curve of the L-lysine HCl salt solution to which weak acid was not added, when it was passed through the strongly basic anion-exchange resin.

The variations of L-lysine concentration (▲), Cl concentration (■) and pH (○) of the effluent solution streamed out from the bottom of the column were measured to obtain a graph shown in FIG. 4.

As a result, it was found that although most of Cl was adsorbed to render Cl/L-Lys of the effluent solution=1.5 mol %, the yield of L-lysine was low, i.e. 54%, and therefore, to put to practical use is difficult.

INDUSTRIAL APPLICABILITY

According to the invention, HCl can be removed efficiently from HCl salt of basic amino acid, and this method is widely utilizable for the production of basic amino acids or basic amino acid salts suitable for each use for medicine, industrial use, feed, food additives and the like.

The invention claimed is:

1. A method of producing a basic amino acid or a basic amino acid salt which comprises preparing a solution comprising a weak acid and a HCl salt of a basic amino acid to provide a weak acid salt of the basic dechlorinating by passing the solution through an anion-exchange resin to prepare said basic amino acid or basic amino acid salt.

2. The method as set forth in claim 1, wherein said basic amino acid is lysine, arginine, histidine, ornithine or hydroxylysine.

3. The method as set forth in claim 1, wherein said weak acid is acetic acid, benzoic acid, caproic acid, formic acid, valeric acid, lactic acid, propionic acid, butyric acid, aspartic acid, glutamic acid, carbonic acid, iodic acid, or fluorine.

4. The method as set forth in claim 1, wherein the anion-exchange resin is in a form of OH, when dechlorinating the solution.

5. The method as set forth in claim 1, wherein said basic amino acid salt is basic amino acid acetate salt.

6. The method as set forth in claim 1, wherein the basic amino acid is L-lysine.

7. The method as set forth in claim 1, wherein the basic amino acid salt is L-lysine acetate salt.

8. The method as set forth in claim 1, wherein the removal efficiency of Cl from the basic amino acid HCl salt is 98.5 mol % or more.

9. The method as set forth in claim 1, wherein the removal efficiency of Cl from the basic amino acid HCl salt is 99.9 mol % or more.

10. The method as set forth in claim 8, wherein the basic amino acid is L-lysine.

11. A method of obtaining a basic amino acid from a HCl salt solution of a basic amino acid which comprises producing a basic amino acid carbonate salt solution by combining a carbonic acid and the HCl salt solution of a basic amino acid, removing chlorine ion from the HCl salt solution of a basic amino acid by passing the basic amino acid carbonate salt solution through anion-exchange resin, and subjecting the basic amino acid carbonate salt solution after said passing to decarbonating treatment.

12. The method as set forth in claim 11, wherein the basic amino acid is L-lysine.

* * * * *